(12) United States Patent
Xiao

(10) Patent No.: US 11,059,787 B2
(45) Date of Patent: Jul. 13, 2021

(54) CRYSTALLINE FORM OF LENVATINIB MESYLATE AND METHODS THEREOF

(71) Applicant: Shenzhen Bolan Pharmaceutical Co., LTD., Shenzhen (CN)

(72) Inventor: Xiangguang Xiao, Shenzhen (CN)

(73) Assignee: SHENZHEN BOLAN PHARMACEUTICAL CO., LTD, Guangdon (CN)

(*) Notice: Subject to any disclaimer, the term of this patent is extended or adjusted under 35 U.S.C. 154(b) by 0 days.

(21) Appl. No.: 16/745,234

(22) Filed: Jan. 16, 2020

(65) Prior Publication Data

US 2021/0139431 A1    May 13, 2021

(30) Foreign Application Priority Data

Nov. 12, 2019 (WO) ............... PCT/CN2019/117626
Dec. 9, 2019 (CN) ....................... 201911252247.1

(51) Int. Cl.
*C07D 215/48* (2006.01)

(52) U.S. Cl.
CPC ....... *C07D 215/48* (2013.01); *C07B 2200/13* (2013.01)

(58) Field of Classification Search
CPC .................. C07D 215/48; C07B 2200/13
See application file for complete search history.

(56) References Cited

U.S. PATENT DOCUMENTS

| 7,612,208 B2 | 11/2009 | Matsushima et al. |
| 10,246,418 B2 | 4/2019 | Chen et al. |
| 2019/0345110 A1* | 11/2019 | Venkata Narasayya ..................... C07D 215/00 |

FOREIGN PATENT DOCUMENTS

| CN | 100569753 C | 12/2009 |
| CN | 109867626 A | 6/2019 |
| CN | 109988112 A | 7/2019 |
| WO | WO-2018054792 A1 | 3/2018 |
| WO | WO-2018196687 A1 | 11/2018 |

* cited by examiner

*Primary Examiner* — Timothy R Rozof
(74) *Attorney, Agent, or Firm* — Morrison & Foerster LLP

(57) ABSTRACT

The present invention provides a novel crystalline form of 4-(3-chloro-4-(cyclopropylaminocarbonyl)aminophenoxy)-7-methoxy-6-quinolinecarboxamide methanesulfonate (i.e., lenvatinib mesylate) and pharmaceutical compositions thereof. Methods of preparing such a crystalline form and uses in treatment are also provided.

16 Claims, 4 Drawing Sheets

CRYSTALLINE FORM OF LENVATINIB MESYLATE AND METHODS THEREOF

CROSS-REFERENCE TO RELATED APPLICATIONS

This application claims priority to PCT International Application No. PCT/CN2019/117626, filed Nov. 12, 2019, and to Chinese Application No. 201911252247.1, filed Dec. 9, 2019, the contents of which applications are herein specifically incorporated by reference in their entireties.

FIELD OF THE INVENTION

The present invention pertains to field of crystals. More particularly, the present invention is directed to a novel crystalline form of lenvatinib mesylate.

BACKGROUND OF THE INVENTION

Lenvatinib is a multiple receptor tyrosine kinase (RTK) inhibitor. Lenvatinib is used in form of the mesylate salt and is marketed in the United States as LENVIMA® by Eisai, Inc. LENVIMA® is approved by the FDA for the treatment of patients with locally recurrent or metastatic, progressive, radioactive iodine-refractory differentiated thyroid cancer. The chemical name of lenvatinib mesylate is 4-(3-chloro-4-(cyclopropylaminocarbonyl)aminophenoxy)-7-methoxy-6-quinolinecarboxamide methanesulfonate, and the structure is shown below:

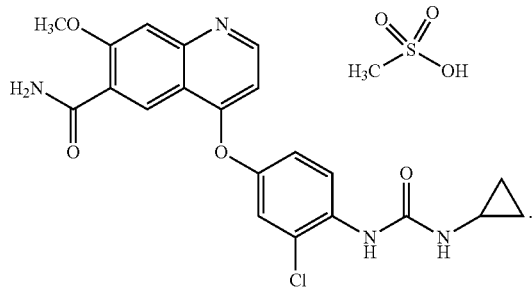

U.S. Pat. No. 7,612,208 (corresponding to CN100569753C) disclosed crystalline Form A, Form B, Form C, Form F and Form I of lenvatinib mesylate. Crystalline Form M of lenvatinib mesylate was disclosed in U.S. Ser. No. 10/246,418. WO2018196687 further disclosed crystalline Form 1 and Form 7, and WO2018054792 disclosed an anhydrous crystalline form, two hydrous crystalline forms and other forms. More recently, CN109988112 disclosed a crystalline form containing 5%-8% water by weight. In addition, various solvates of lenvatinib mesylate (with organic solvents, such as dimethyl sulfoxide) have been studies and crystallized.

Since different crystalline forms of the same compound are different in solubility and stability, absorption and bioavailability, and therapeutic effect will be affected. Hence, there is a need to discover suitable crystalline forms to optimize the therapeutic effect of lenvatinib mesylate.

SUMMARY OF THE INVENTION

The present invention relates to a novel crystalline form of lenvatinib mesylate. In one aspect, the present invention discloses a novel crystalline form, designated as Form XI, of lenvatinib mesylate, that is, 4-(3-chloro-4-(cyclopropylaminocarbonyl)aminophenoxy)-7-methoxy-6-quinolinecarboxamide methanesulfonate.

The present invention also discloses pharmaceutical compositions comprising the crystalline form of 4-(3-chloro-4-(cyclopropylaminocarbonyl)aminophenoxy)-7-methoxy-6-quinolinecarboxamide methanesulfonate along with one or more pharmaceutically acceptable excipients.

In another aspect, the present invention provides a method for preparation of the crystalline form of 4-(3-chloro-4-(cyclopropylaminocarbonyl)aminophenoxy)-7-methoxy-6-quinolinecarboxamide methanesulfonate.

In yet another aspect, the crystalline form and pharmaceutical compositions described herein are useful in treating diseases, disorders or conditions, where lenvatinib mesylate is useful as an angiogenesis inhibitor, such as a multiple receptor tyrosine kinase (RTK) inhibitor. In some embodiments, the crystalline form and the pharmaceutical compositions are used in treating cancers, for example, a thyroid cancer.

DETAILED DESCRIPTION OF THE INVENTION

Figure 1:
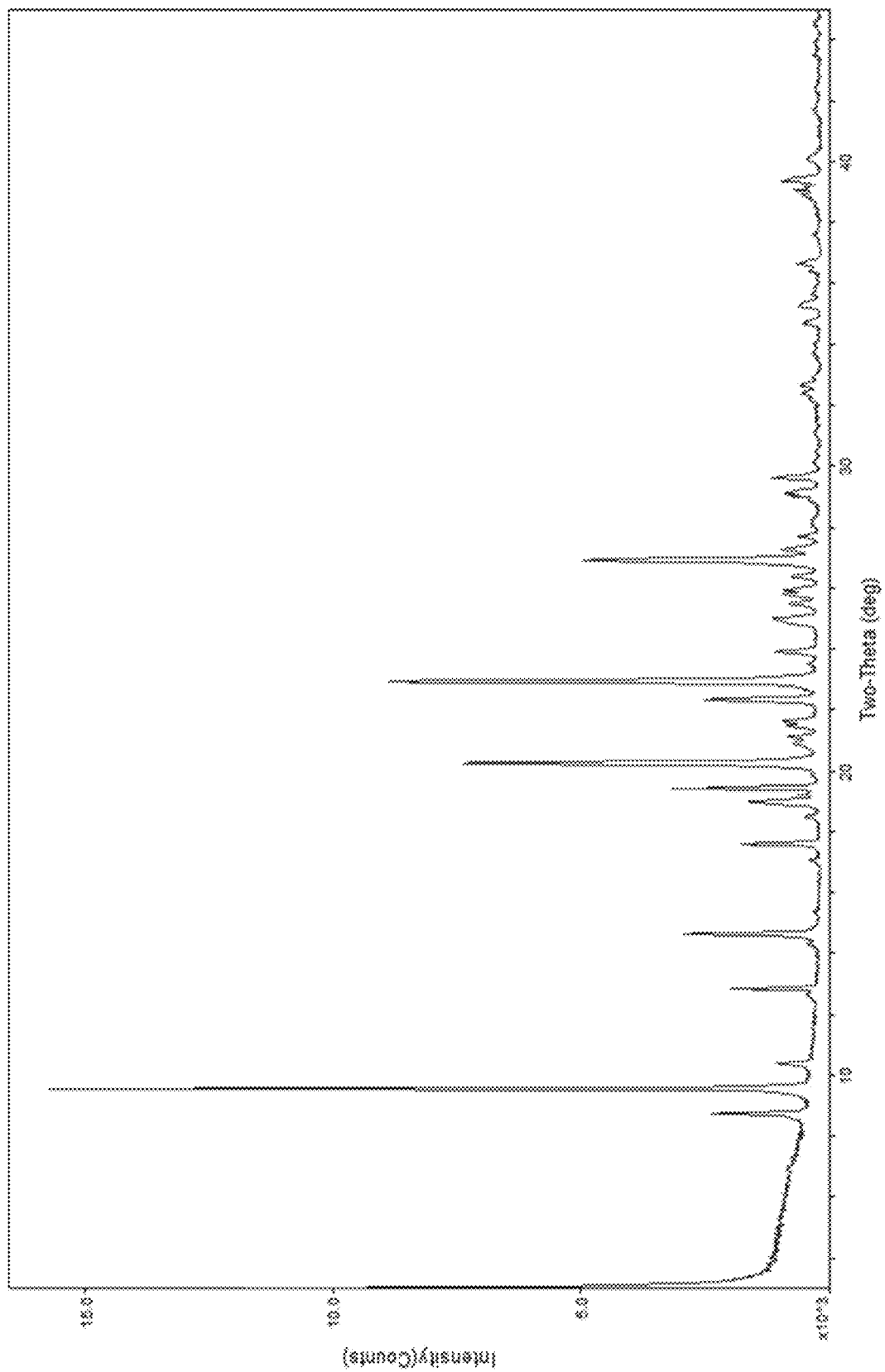
FIG. 1 shows an X-ray powder diffraction (XRPD) pattern of Form XI.

The present invention relates to a crystalline form of 4-(3-chloro-4-(cyclopropylaminocarbonyl)aminophenoxy)-7-methoxy-6-quinolinecarboxamide methanesulfonate (Form XI) and pharmaceutical compositions thereof. Also provided herein are processes for preparation of Form XI and its uses in treatment.

As used herein and in the appended claims, the singular forms "a", "an" and "the" include plural forms, unless the context clearly dictates otherwise.

As used herein, and unless otherwise specified, the terms "about" and "approximately," when used in connection with doses, amounts, molar percent, or weight percent of ingredients of a composition or a dosage form, mean a dose, amount, molar percent, or weight percent that is recognized by those of ordinary skill in the art to provide a pharmacological effect equivalent to that obtained from the specified dose, amount, molar percent, or weight percent. Specifically, the terms "about" and "approximately," when used in this context, contemplate a dose, amount, molar percent, or weight percent within 15%, within 10%, within 5%, within 4%, within 3%, within 2%, within 1%, or within 0.5% of the specified dose, amount, molar percent, or weight percent.

As used herein, "therapeutically effective amount" indicates an amount that results in a desired pharmacological and/or physiological effect for the condition. The effect may be prophylactic in terms of completely or partially preventing a condition or symptom thereof and/or may be therapeutic in terms of a partial or complete cure for the condition and/or adverse effect attributable to the condition.

As used herein, the term "pharmaceutically acceptable excipient," and cognates thereof, refers to adjuvants, binders, diluents, etc. known to the skilled artisan that are suitable for administration to an individual (e.g., a mammal or non-mammal). Combinations of two or more excipients are also contemplated. The pharmaceutically acceptable excipient(s) and any additional components, as described herein, should be compatible for use in the intended route of administration (e.g., oral, parenteral) for a particular dosage form, as would be recognized by the skilled artisan.

The terms "treat," "treating," and "treatment" are meant to include alleviating or abrogating a disorder, disease, or condition, or one or more of the symptoms associated with the disorder, disease, or condition; or to slowing the progression, spread or worsening of a disease, disorder or condition or of one or more symptoms thereof. Often, the beneficial effects that a subject derives from a therapeutic agent do not result in a complete cure of the disease, disorder or condition.

The term "subject" refers to an animal, including, but not limited to, a primate (e.g., human), monkey, cow, pig, sheep, goat, horse, dog, cat, rabbit, rat, or mouse. The terms "subject" and "patient" are used interchangeably herein in reference, for example, to a mammalian subject, such as a human.

As used herein, the term "substantially as shown in" when referring, for example, to an XRPD pattern, a TGA graph or a DSC graph, includes a pattern or graph that is not necessarily identical to those depicted herein, but that falls within the limits of experimental error or deviations when considered by one of ordinary skill in the art.

Crystalline Form

The present invention provides a novel crystalline form (Form XI) of 4-(3-chloro-4-(cyclopropylaminocarbonyl) aminophenoxy)-7-methoxy-6-quinolinecarboxamide methanesulfonate. Crystalline forms described herein can have a purity of at least 80%, 85%, 90%, 91%, 92%, 93%, 94%, 95%, 96%, 97%, 98%, 99%, 99.5%, 99.8%, or 99.9%.

It has been found that 4-(3-chloro-4-(cyclopropylaminocarbonyl)aminophenoxy)-7-methoxy-6-quinolinecarboxamide methanesulfonate is able to form solvates in crystallization. Examples of such solvates include solvates from water, solvates from alcohols such as methanol, ethanol, propan-1-ol or propan-2-ol; solvates from organic esters such as ethyl acetate; solvates from acetonitrile; and solvates from ketones. In some embodiments of the present invention, the crystalline form provided is in a hydrous form. The molar ratio of water to 4-(3-chloro-4-(cyclopropylaminocarbonyl)aminophenoxy)-7-methoxy-6-quinolinecarboxamide methanesulfonate could vary in a range from 0.25:1 to 2.5:1. In some embodiments, the molar ratio is in a range of 0.5:1 to 1.5:1. In specific embodiments, the molar ratio is about 1:1.

The crystalline form provided herein can be characterized by Karl Fischer Titration (KF) for measurement of water contents. In some embodiments, the crystalline form provided comprises about 1.7-4.9 wt % of water. In some embodiments, the crystalline form provided comprises about 3.23 wt of water.

The crystalline form provided herein can be characterized by an X-ray powder diffraction (XRPD) pattern having characteristic peaks, in terms of 2θ. The relative intensities of the peaks can vary, depending upon the sample preparation technique, the sample mounting procedure and the particular instrument employed. Moreover, instrument variation and other factors can affect the 2-theta values. In some embodiments, the XRPD peak assignments can vary by plus or minus about 0.2°.

In some embodiments, the crystalline form of 4-(3-chloro-4-(cyclopropylaminocarbonyl)aminophenoxy)-7-methoxy-6-quinolinecarboxamide methanesulfonate is characterized by an XRPD pattern comprising a peak at a diffraction angle (2θ±0.2°) of 8.713°. In some embodiments, the XRPD pattern further comprises one or more peaks at diffraction angles (2θ±0.2°) selected from the group consisting of 10.366, 12.819° and 14.615°. In some embodiments, the XRPD pattern further comprises one or more peaks at diffraction angles (2θ±0.2°) selected from the group consisting of 9.520°, 19.400°, 20.218°, 22.895° and 26.876°. In some embodiments, the crystalline form of 4-(3-chloro-4-(cyclopropylaminocarbonyl)aminophenoxy)-7-methoxy-6-quinolinecarboxamide methanesulfonate is characterized by an XRPD pattern comprising one or more peaks at diffraction angles (2θ±0.2°) of 8.713°, 10.366°, 12.819°, 14.615°, 9.520°, 19.400°, 20.218°, 22.895° and 26.876°.

In some embodiments, the crystalline form is characterized by an XRPD pattern substantially as shown in FIG. 1.

Figure 2:
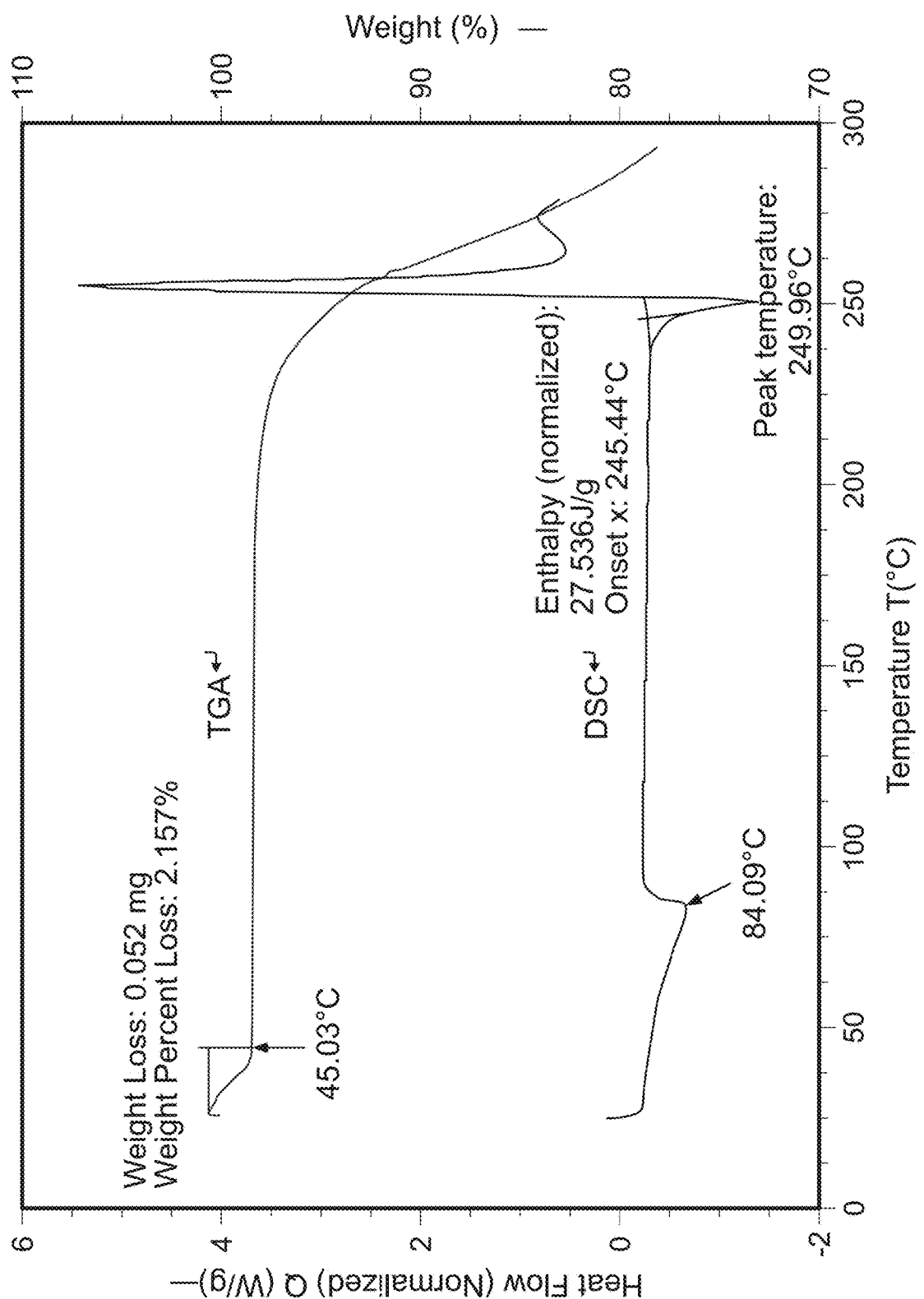
FIG. 2 shows a graph of thermal gravimetric analysis (TGA) and differential scanning calorimetry (DSC) of Form XI.

The crystalline form provided herein can also be identified by its characteristic thermal gravimetric analysis (TGA) and/or differential scanning calorimetry (DSC) trace. In some embodiments, the crystalline form has characteristic TGA and/or DSC patterns substantially as shown in FIG. 2.

Compositions

When the crystalline form of the present invention are to be used as a medicament, it will normally be mixed with suitable additives for use as a formulation. Such additives may include excipients, binders, lubricants, disintegrators, coloring agents, taste correctives, emulsifiers, surfactants, dissolving aids, suspending agents, isotonizing agents, buffering agents, antiseptics, antioxidants, stabilizers, absorption accelerators and the like which are commonly used in pharmaceuticals, and they may be added in appropriate combinations as desired.

In some embodiments, the present invention provides pharmaceutical compositions comprising the crystalline form (Form XI) of 4-(3-chloro-4-(cyclopropylaminocarbonyl)aminophenoxy)-7-methoxy-6-quinolinecarboxamide methanesulfonate, together with one or more pharmaceutically acceptable excipients.

Exemplary excipients may include, but not limited to, lactose, white soft sugar, glucose, corn starch, mannitol, sorbitol, starch, alpha starch, dextrin, crystalline cellulose, soft silicic anhydride, aluminum silicate, calcium silicate, magnesium aluminometasilicate, and calcium hydrogenphosphate.

Exemplary binders may include, but not limited to, polyvinyl alcohol, methylcellulose, ethylcellulose, gum Arabic, tragacanth, gelatin, shellac, hydroxypropylmethylcellulose, hydroxypropylcellulose, carboxymethylcellulose sodium, polyvinylpyrrolidone, macrogol, and the like. Exemplary lubricants may include, but not limited to, magnesium stearate, calcium stearate, sodium stearyl fumarate, talc, polyethylene glycol, colloidal silica, and the like. Exemplary disintegrators may include, but not limited to, crystalline cellulose, agar, gelatin, calcium carbonate, sodium hydrogencarbonate, calcium citrate, dextrin, pectin, low-substituted hydroxypropylcellulose, carboxymethylcellulose, carboxymethylcellulose calcium, croscarmellose sodium, carboxymethyl starch, and carboxymethyl starch sodium, and the like.

Also provided are formulations comprising the crystalline form (Form XI) of 4-(3-chloro-4-(cyclopropylaminocarbonyl)aminophenoxy)-7-methoxy-6-quinolinecarboxamide methanesulfonate in the form of an oral preparation such as a tablet, powder, granule, capsule, syrup, lozenge or inhalant; an external preparation such as a suppository, ointment, eye salve, tape, eye drop, nasal drop, ear drop, pap or lotion; or an injection.

Pharmaceutically acceptable compositions include solid, semi-solid, liquid and aerosol dosage forms, such as tablet, capsule, powder, liquid, suspension, suppository, and aerosol forms. The crystalline form disclosed and/or described herein can also be administered in sustained or controlled release dosage forms (e.g., controlled/sustained release pill, depot injection, osmotic pump, or transdermal (including electrotransport) patch forms) for prolonged timed, and/or pulsed administration at a predetermined rate. In some embodiments, the compositions are provided in unit dosage forms suitable for single administration of a precise dose.

In some embodiments, the compositions will take the form of a pill or tablet and thus the composition may contain, along with a crystalline form disclosed and/or described herein, one or more of a diluent (e.g., lactose, sucrose, dicalcium phosphate), a lubricant (e.g., magnesium stearate), and/or a binder (e.g., starch, gum acacia, polyvinylpyrrolidine, gelatin, cellulose, cellulose derivatives). Other solid dosage forms include a powder, marume, solution or suspension (e.g., in propylene carbonate, vegetable oils or triglycerides) encapsulated in a gelatin capsule.

Liquid pharmaceutically administrable compositions can, for example, be prepared by dissolving, dispersing or suspending etc. a crystalline form disclosed and/or described herein and optional pharmaceutical additives in a carrier (e.g., water, saline, aqueous dextrose, glycerol, glycols, ethanol or the like) to form a solution or suspension. Injectables can be prepared in conventional forms, either as liquid solutions or suspensions, as emulsions, or in solid forms suitable for dissolution or suspension in liquid prior to injection. The percentage of the crystalline form contained in such parenteral compositions depends, for example, on the physical nature of the crystalline form, the activity of the crystalline form, and the needs of the subject. However, percentages of active ingredient of 0.01% to 10% in solution are employable, and may be higher if the composition is a solid which will be subsequently diluted to another concentration. In some embodiments, the composition will comprise from about 0.2 to 2% of a crystalline form disclosed and/or described herein in solution.

Pharmaceutical compositions of the crystalline form and compositions described herein may also be administered to the respiratory tract as an aerosol or solution for a nebulizer, or as a microfine powder for insufflation, alone or in combination with an inert carrier such as lactose. In such a case, the particles of the pharmaceutical composition may have diameters of less than 50 microns, or in some embodiments, less than 10 microns.

In addition, pharmaceutical compositions can include a crystalline form disclosed and/or described herein and one or more additional medicinal agents, pharmaceutical agents, adjuvants, and the like.

Variations of compositions described herein can be prepared using additives and methods including, without limitation, as described in U.S. Pat. No. 7,612,208, which is incorporated by reference herein in its entirety.

Methods of Preparation

In another aspect, the present invention provides a process for preparing a novel crystalline form (Form XI) of 4-(3-chloro-4-(cyclopropylaminocarbonyl)aminophenoxy)-7-methoxy-6-quinolinecarboxamide methanesulfonate. In some embodiments, the process comprises the following steps:

(i) dissolving 4-(3-chloro-4-(cyclopropylaminocarbonyl) aminophenoxy)-7-methoxy-6-quinolinecarboxamide methanesulfonate in a mixture of solvents to obtain a solution;
(ii) adding an additional solvent into the solution obtained from step (i);
(iii) stirring the solution of step (ii) at room temperature for a period of time; and
(iv) collecting the crystalline form.

In some embodiments of any of the methods of preparing the crystalline forms provided herein, 4-(3-chloro-4-(cyclopropylaminocarbonyl)aminophenoxy)-7-methoxy-6-quinolinecarboxamide methanesulfonate is added to a solvent. The solvent in the process of the present invention may be an organic solvent or an aqueous solvent or mixtures thereof. The solvents may be selected from the group consisting of water; alcohols (such as methanol, and ethanol); acids (such as acetic acid); acetonitrile; and any mixtures thereof.

In some embodiments, an organic solution or an aqueous solution comprises two or more solvents. In some embodiments, the solvents comprise water and one selected from the group consisting of alcohols (such as methanol, and ethanol); acids (such as acetic acid); acetonitrile; and any mixtures thereof. In some embodiments, the solvents comprise water and acetonitrile. The ratio of solvents in mixtures varies. In some embodiments, two solvents in a mixture may be present in a molar or volume ratio that varies in the range of 1:100 to 100:1, 1:10 to 10:1, or 1:3 to 3:1. In some embodiments, two solvents may be present in a molar or volume ratio of about 1:100, about 1:50, about 1:20, about 1:10, about 1:5, about 1:3, about 1:2, about 1:1, about 2:1, about 3:1, about 5:1, about 10:1, about 20:1, about 50:1, or about 100:1. In some specific embodiments, a mixture includes water and acetonitrile at a volume ratio of about 6:47. In some specific embodiments, a mixture includes water and acetonitrile at a volume ratio of about 6:27.

The solution may be heated to a temperature between about 37° C. to about 80° C. until a clear solution is obtained. In some embodiments, the solution is heated to a temperature of about 37° C., about 40° C., about 50° C., about 55° C., about 58° C., about 60° C., about 65° C., about 70° C., or about 80° C. In some embodiments, the solution is heated to a temperature of about 55° C. until a clear solution is obtained. In some embodiments, the solution is heated to a temperature higher than about 58° C. In some embodiments, the solution is cooled down to about 40° C. after the clear solution is obtained.

After dissolving 4-(3-chloro-4-(cyclopropylaminocarbonyl)aminophenoxy)-7-methoxy-6-quinolinecarboxamide methanesulfonate in the mixture of solvents, an additional solvent can be slowly added, for example, drop by drop. Suitable additional solvents can be used include, but are not limited to, ethyl acetate, methyl tert-butyl ether, and ether. In some embodiments, ethyl acetate is added into a mixture of water and acetonitrile.

The resulting solution after the additional solvent is added may be stirred for a period of 1 hour to 7 days at a temperature lower than the heated temperature before the crystalline form is collected. The temperature can range from 10-40° C., for example, at about 10° C., at about 20° C., at about 25° C., or at about 37° C. In some embodiments, the solution is stirred for a period of about 1 day, about 2 days, about 3 days, about 4 days, about 5 days, about 6 days, or about 7 days. In some embodiments, the solution is stirred for a period of about 2 hours, about 12 hours, about 16 hours, about 18 hours, about 20 hours, about 24 hours, about 36 hours, about 48 hours, about 60 hours, about 72 hours, or about 90 hours. In some embodiments, the solution is stirred for a period of time at a temperature in the range of about 20° C. to about 40° C., about 20° C. to about 30° C., or about 30° C. to about 40° C. In some embodiments, the solution is stirred for a period of about 18-20 hours at room temperature (e.g., 25° C.).

The crystalline form prepared may be evaluated for its physicochemical parameters using methods known in the art, including through analytical techniques such as X-ray powder diffraction (XRPD, also referred to as PXRD), differential scanning calorimetry (DSC), thermal gravimetric analysis (TGA), infrared (IR) spectroscopy, and the like.

Methods of Use

In yet another aspect, the present invention provides methods for treating diseases or disorders, or uses in treating diseases or disorders The crystalline forms and compositions of the present invention may be used in treating all indications in which 4-(3-chloro-4-(cyclopropylaminocarbonyl) aminophenoxy)-7-methoxy-6-quinolinecarboxamide methanesulfonate is used, including, without limitation, any of the disease or conditions described in U.S. Pat. No. 7,612,208, which is hereby incorporated by reference in its entirety. In specific embodiments, provided are methods of treating all indications in which LENVIMA is used.

The crystalline form and compositions disclosed and/or described herein may be useful as an angiogenesis inhibitor. In some embodiments, provided are methods of treating or preventing a disease for which angiogenesis inhibition is effective, an angiogenesis inhibitor, an anti-tumor agent, a therapeutic agent for angioma, a cancer metastasis inhibitor, a therapeutic agent for retinal neovascularization, a therapeutic agent for diabetic retinopathy, a therapeutic agent for an inflammatory disease, a therapeutic agent for an inflammatory disease selected from the group consisting of deformant arthritis, rheumatoid arthritis, psoriasis and delayed hypersensitivity reaction, and a therapeutic agent for atherosclerosis.

In some embodiments, the crystalline form and compositions disclosed and/or described herein are used as an anti-tumor agent. Exemplary cancers include, but are not limited to, a thyroid cancer, a pancreatic cancer, a gastric cancer, a colon cancer, a breast cancer, a prostate cancer, a lung cancer, a liver cancer, a renal cancer, a brain tumor, a blood cancer or an ovarian cancer. In some embodiments, cancer is a thyroid cancer, a liver cancer, or a renal cancer.

Further, the crystalline form and compositions disclosed and/or described herein may exhibit a strong inhibitory activity for c-Kit kinase, and be useful as an anti-cancer agent for a cancer which has undergone a malignant alteration due to activation of c-Kit kinase (for example, acute myelogenous leukemia, mast cell leukemia, a small cell lung cancer, GIST, a testicular tumor, an ovarian cancer, a breast cancer, a brain tumor, neuroblastoma or a colon cancer). The crystalline form and compositions disclosed and/or described herein are also useful as a therapeutic agent for a disease such as mastocytosis, allergy or asthma that is considered to be caused by c-Kit kinase.

In some embodiments, provided are methods of treating diseases, disorders or conditions where the crystalline form and compositions disclosed and/or described herein are used as a multiple-receptor tyrosine kinase (RTK) inhibitor. In some embodiments, provided are methods of treating endometrial carcinoma, hepatocellular carcinoma, renal cell carcinoma, and/or thyroid cancer. In some embodiments, provided are methods of treating invasive and differentiated thyroid cancer. In some embodiments, provided are methods of treating locally recurrent or metastatic, progressive, radioactive iodine-refractory differentiated thyroid cancer. In some embodiments, provided are methods of treating advanced renal cell carcinoma (RCC) following one prior anti-angiogenic therapy, in combination with everolimus. In some embodiments, provided are methods of treating unresectable hepatocellular carcinoma (HCC) for the first-line treatment.

Provided are methods of treating or preventing any of the diseases, disorders or conditions described herein in a subject in need thereof, comprising administering to the subject a therapeutically effective amount of the crystalline form or pharmaceutical compositions provided herein. Also provided is a crystalline form provided herein for use the manufacture of a medicament for treating or preventing any of the diseases, disorders or conditions described herein in a subject in need thereof.

Dosages

The crystalline form and compositions disclosed and/or described herein are administered at a therapeutically effective dosage, e.g., a dosage sufficient to provide treatment for the disease state, in a subject (e.g., patients) in need. While human dosage levels have yet to be optimized for the chemical entities described herein, generally, a daily dose ranges from about 0.01 to 100 mg/kg of body weight; in some embodiments, from about 0.05 to 10.0 mg/kg of body weight, and in some embodiments, from about 0.10 to 1.4 mg/kg of body weight. Thus, for administration to a 70 kg person, in some embodiments, the dosage range would be about from 0.7 to 7000 mg per day; in some embodiments, about from 3.5 to 700.0 mg per day, and in some embodiments, about from 7 to 100.0 mg per day. The amount of the chemical entity administered will be dependent, for example, on the subject and disease state being treated, the severity of the affliction, the manner and schedule of administration and the judgment of the prescribing physician. For example, an exemplary dosage range for oral administration is from about 5 mg to about 500 mg per day, and an exemplary intravenous administration dosage is from about 5 mg to about 500 mg per day, each depending upon the pharmacokinetics.

A daily dose is the total amount administered in a day. A daily dose may be, but is not limited to be, administered each day, every other day, each week, every 2 weeks, every month, or at a varied interval. In some embodiments, the daily dose is administered for a period ranging from a single day to the life of the subject. In some embodiments, the daily dose is administered once a day. In some embodiments, the daily dose is administered in multiple divided doses, such as in 2, 3, or 4 divided doses. In some embodiments, the daily dose is administered in 2 divided doses.

Administration of the crystalline form and compositions described herein can be via any accepted mode of administration for therapeutic agents including, but not limited to, oral, sublingual, subcutaneous, parenteral, intravenous, intranasal, topical, transdermal, intraperitoneal, intramuscular, intrapulmonary, vaginal, rectal, or intraocular administration.

In some embodiments, the crystalline form or composition is administered orally or intravenously. In some embodiments, the crystalline form or composition disclosed and/or described herein is administered orally.

In specific embodiments, the crystalline form and compositions disclosed and/or described herein are administered at a therapeutically effective dosage of 24 mg orally once daily. In other specific embodiments, they are administered at a therapeutically effective dosage of 14 mg orally once daily in patients with severe renal or hepatic impairment. In certain embodiments, they are administered at a therapeutically effective dosage of 18 mg orally once daily with 5 mg everolimus orally once daily. The dosage can be based on actually body weight. To give two examples, they are administered at 12 mg orally once daily for patents greater than or equal to 60 kg, or at 8 mg orally once daily for patients less than 60 kg.

Kits

Also provided are articles of manufacture and kits containing any of the crystalline forms or compositions provided herein. The article of manufacture may comprise a container with a label. Suitable containers include, for example, bottles, vials, and test tubes. The containers may be formed from a variety of materials such as glass or plastic. The container may hold a pharmaceutical composition provided herein. The label on the container may indicate that the pharmaceutical composition is used for preventing, treating or suppressing a condition described herein, and may also indicate directions for either in vivo or in vitro use.

In one aspect, provided herein are kits containing a crystalline form or composition described herein and instructions for use. The kits may contain instructions for use in the treatment of any disease provided herein in a subject in need thereof. A kit may additionally contain any materials or equipment that may be used in the administration of the crystalline form or composition, such as vials, syringes, or IV bags. A kit may also contain sterile packaging.

Certain specific aspects and embodiments of the present invention will be explained in more detail with reference to the following examples, which are provided only for purposes of illustration and should not be construed as limiting the scope of the invention in any manner.

The following Examples will further illustrate the present invention, which by no means limit the scope of the invention.

EXAMPLES

Preparation of Crystalline Form

Example 1

To a mixture of water (3 mL) and acetonitrile (23.4 mL), 175.8 mg of 4-(3-chloro-4-(cyclopropylaminocarbonyl)aminophenoxy)-7-methoxy-6-quinolinecarboxamide methanesulfonate was added at 37° C. to dissolve. 33 mL of ethyl acetate was then added slowly drop by drop into the reaction mixture, which was also stirred and cooled down to room temperature (about 25° C.) to obtain a suspension. Such a suspension was stirred for 18 hours and then was filtered to give the crystalline form XI.

Example 2

To a mixture of water (6 mL) and acetonitrile (27 mL), 1.018 g of 4-(3-chloro-4-(cyclopropylaminocarbonyl)aminophenoxy)-7-methoxy-6-quinolinecarboxamide methanesulfonate was added. The mixture was heated up to 55° C. until a clear solution was obtained, and then was cooled down to 40° C. 66 mL of ethyl acetate was then added slowly drop by drop into the reaction mixture, which was also stirred and cooled down to room temperature (about 25° C.) to obtain a suspension. Such a suspension was stirred for 20 hours and then was filtered to give the crystalline form XI (yield: 85%).

Characterization of Crystalline Form

Example 3

X-ray Powder Diffraction (XRPD): Form XI were analyzed using Bruker D8 Advance X-ray Diffractometer (Bruker, GER). The X-ray source is a Cu tube that was operated at 40 kV and 40 mA. Powder samples were prepared on a zero-background Si holder using light manual pressure to keep the sample surfaces flat. Each sample was analyzed from 3 to 45°2θ with an effective step size of 0.02°2θ and 0.2 s exposure time.

The representative XRPD pattern is presented in FIG. 1. The raw data are shown in Table 1 below. 2Theta values are listed with their d values and relative intensities.

TABLE 1

| Angle | d Value | Relative Intensity |
| --- | --- | --- |
| 8.713° | 10.14117 Å | 12.0% |
| 9.520° | 9.28272 Å | 100.0% |
| 10.366° | 8.52670 Å | 4.1% |
| 12.606° | 7.01655 Å | 1.1% |
| 12.819° | 6.90016 Å | 12.9% |
| 14.274° | 6.20016 Å | 1.5% |
| 14.615° | 6.05623 Å | 17.4% |
| 15.312° | 5.78207 Å | 0.7% |
| 17006° | 5.20954 Å | 1.1% |
| 17.557° | 5.04737 Å | 11.9% |
| 18.465° | 4.80126 Å | 1.6% |
| 18.952° | 4.67886 Å | 8.5% |
| 19.212° | 4.61609 Å | 1.5% |
| 19.400° | 4.57171 Å | 23.0% |
| 19.842° | 4.47105 Å | 0.6% |
| 20.218° | 4.38863 Å | 51.6% |
| 20.862° | 4.25452 Å | 2.7% |
| 21.081° | 4.21087 Å | 3.5% |
| 21.442° | 4.14077 Å | 3.5% |
| 21.600° | 4.11096 Å | 4.3% |
| 22.295° | 3.98427 Å | 15.4% |
| 22.895° | 3.88118 Å | 63.9% |
| 23.468° | 3.78767 Å | 1.0% |
| 23.868° | 3.72508 Å | 5.8% |
| 24.947° | 3.56646 Å | 5.9% |
| 25.444° | 3.49791 Å | 3.8% |
| 25.812° | 3.44882 Å | 2.1% |
| 26.347° | 3.37999 Å | 3.9% |
| 26.876° | 3.31466 Å | 36.3% |
| 27.228° | 3.27264 Å | 5.4% |
| 27.659° | 3.22252 Å | 2.7% |
| 28.122° | 3.17050 Å | 0.6% |
| 28.996° | 3.07692 Å | 4.3% |
| 29.113° | 3.06480 Å | 4.3% |
| 29.587° | 3.01680 Å | 7.9% |
| 30.070° | 2.96941 Å | 0.5% |
| 30.478° | 2.93065 Å | 0.6% |
| 31.011° | 2.88148 Å | 0.8% |
| 31.839° | 2.80842 Å | 0.4% |
| 32.346° | 2.76554 Å | 2.6% |
| 32.617° | 2.74312 Å | 3.2% |
| 32.8740° | 2.72225 Å | 1.5% |
| 33.694° | 2.65791 Å | 0.6% |
| 33.943° | 2.63893 Å | 0.7% |
| 34.643° | 7.58723 Å | 2.6% |
| 35.234° | 2.54513 Å | 3.4% |
| 35.625° | 2.51811 Å | 1.3% |
| 35.851° | 2.50277 Å | 0.8% |
| 36.392° | 2.46679 Å | 1.8% |
| 36.608° | 2.45276 Å | 4.0% |
| 37.541° | 2.39390 Å | 0.7% |
| 38.255° | 2.35081 Å | 0.3% |
| 38.873° | 2.31489 Å | 2.6% |
| 39.037° | 2.30551 Å | 4.0% |
| 39.327° | 2.28918 Å | 6.6% |
| 40.048° | 2.24962 Å | 1.5% |
| 41.6340° | 2.16750 Å | 0.8% |
| 42.3470° | 2.13267 Å | 0.7% |

TABLE 1-continued

| Angle | d Value | Relative Intensity |
|---|---|---|
| 43.4620° | 2.08047 Å | 1.4% |
| 43.806° | 2.06493 Å | 0.5% |
| 44.476° | 2.03539 Å | 0.8% |

Example 4

Thermal gravimetric analysis (TGA): Form XI was analyzed using a TA Instruments Discovery 55 (TA, US). The instrument balance was calibrated using standard weights and the temperature calibration was performed using nickel. The nitrogen purge was 40 mL per minute at the balance and 60 mL per minute at the furnace. Each sample was placed into a pre-tared platinum pan and heated from 25° C. to 300° C. at a rate of 10° C./minute.

Differential scanning calorimetry (DSC): Form XI was analyzed using a TA Instruments Discovery 2500 (TA, US). Calibration of the instrument temperature and cell constant was performed using indium. The DSC cell was kept under a nitrogen purge of 60 mL per minute during each analysis. The sample was placed in a Tzero aluminum pan and was heated from 25° C. to 280° C. at a rate of 10° C./minute.

The representative TGA and DSC graphs of Form XI are depicted in FIG. 2. The results indicate that Form XI is a hydrate.

Example 5

The water content of Form XI was analyzed by using 870 KF Titrino Plus (Metrohm, Swiss). The sample with known weight was added into the pre-equilibrated methanol and then titrated with the Karl Fischer reagent automatically. The result shows that the water content of Form XI is about 3.23 wt %, and further indicates that the molar ratio of water to 4-(3-chloro-4-(cyclopropylaminocarbonyl)aminophenoxy)-7-methoxy-6-quinolinecarboxamide methanesulfonate is about 1:1.

Example 6

Figure 3:
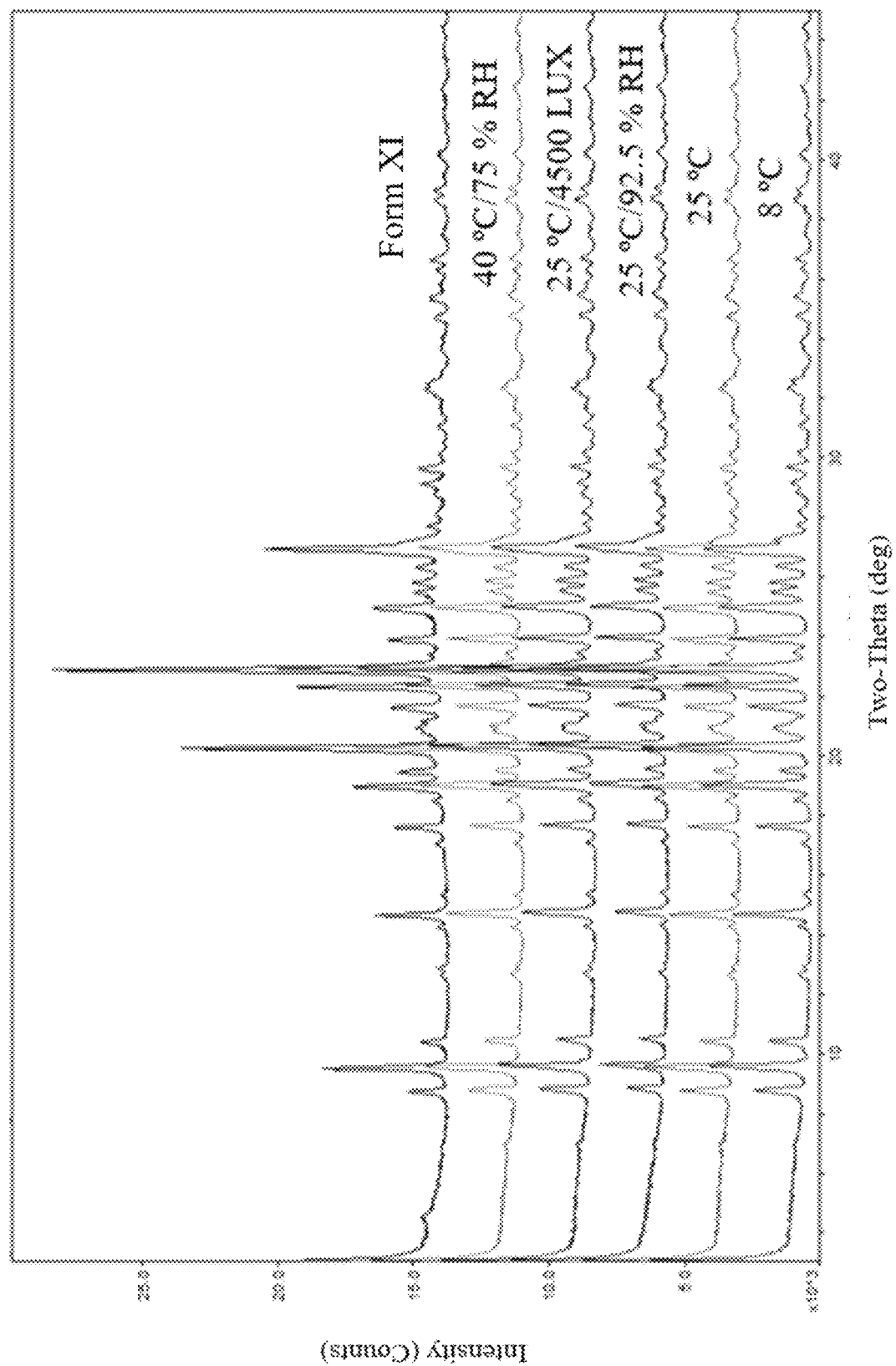
FIG. 3 illustrates the stability of Form XI under various storage conditions for 15 days.
Figure 4:
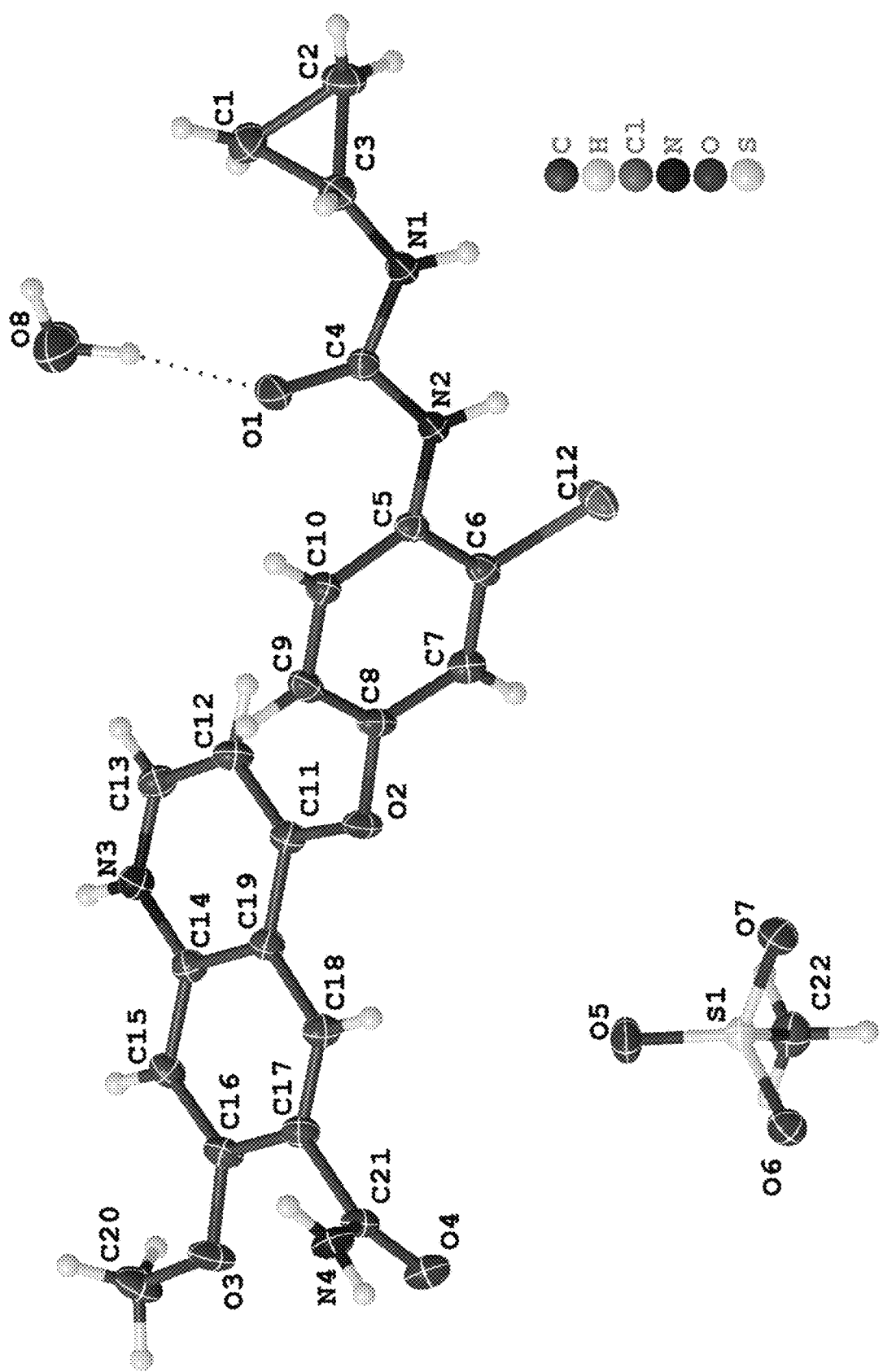
FIG. 4 shows the single crystal structure of Form XI.

The stability of Form XI was measured after being stored for 15 days under the following conditions: 8° C., 25° C., 25° C./92.5% RH, 25° C./4500 LUX and 40° C./75% RH. The results showed that Form XI was stable under those storage conditions. The comparison of the XRPD pattern is shown in FIG. 3.

Example 7

The solubility of Form XI was measured as compared to the previously reported Form A and Form C in U.S. Pat. No. 7,612,208. Form XI, Form A and Form C solids were gradually added into water with 1% polyvinyl alcohol until the solids could not dissolve completely and stay in suspension for 5 hours. The solubility data were then measured and are shown in Table 2 below. The results showed that the solubility of Form XI was greatly improved as compared to that of Form A and Form C.

TABLE 2

| Crystalline Form | Solubility (mg/mL) |
|---|---|
| Form XI | 26.65 |
| Form A | 11.75 |
| Form C | 16.175 |

Example 8

The single crystal of Form XI was obtained by vapor diffusion. The saturated water/acetonitrile solution of Lenvatinib was left under the ethyl acetate vapor environment until the single crystal was obtained. Single crystal X-ray diffraction data were collected on a Rigaku XtaLAB Pro diffractometer. The structure was solved and refined using Olex2 program. The structure indicated Form XI was a monohydrate and the experimental XRPD matched with the calculated XRPD from the single crystal structure.

TABLE 3

| Crystal data and structure refinement | |
|---|---|
| Empirical formula | $C_{22}H_{25}N_4O_8SCl$ |
| Formula weight | 540.98 |
| Temperature/K | 150 |
| Crystal system | triclinic |
| Space group | P-1 |
| a/Å | 9.40780(11) |
| b/Å | 10.40219(12) |
| c/Å | 13.35224(15) |
| α/° | 74.5417(10) |
| β/° | 73.8611(10) |
| γ/° | 87.6221(9) |
| Volume/Å$^3$ | 1209.02(3) |
| Z | 2 |
| $\rho_{calc}$ g/cm$^3$ | 1.4859 |
| μ/mm$^{-1}$ | 2.701 |
| F(000) | 567.3 |
| Radiation | Cu Kα (λ = 1.54184) |
| 2θ range for data collection/° | 7.14 to 148.04 |
| Index ranges | $-11 \leq h \leq 11, -12 \leq k \leq 12, -16 \leq l \leq 16$ |
| Reflections collected | 29050 |
| Independent reflections | 4797 [$R_{int}$ = 0.0487, $R_{sigma}$ = 0.0263] |
| Data/restraints/parameters | 4797/0/343 |
| Goodness-of-fit on F$^2$ | 1.043 |
| Final R indexes [I ≥ 2σ (I)] | $R_1$ = 0.0380, $wR_2$ = 0.1032 |
| Final R indexes [all data] | $R_1$ = 0.0389, $wR_2$ = 0.1039 |
| Largest diff. peak/hole/e Å$^{-3}$ | 0.41/−0.60 |

TABLE 4

| Fractional Atomic Coordinates (×10$^4$) | | | |
|---|---|---|---|
| Atom | x | y | z |
| S1 | 4085.1(4) | 2045.4(4) | 2304.2(3) |
| C12 | 3292.5(5) | 3652.2(4) | 9457.0(3) |
| O2 | 306.7(12) | 6357.0(12) | 7047.5(9) |
| O5 | 3994.0(15) | 3479.4(12) | 1935.5(11) |
| O6 | 2711.3(13) | 1331.2(12) | 2409.3(9) |
| O7 | 4544.4(15) | 1610.7(13) | 3295.9(10) |
| N3 | 1780.7(15) | 9388.5(14) | 4308.4(11) |
| C11 | 854.4(17) | 7361.6(16) | 6171.5(12) |
| C13 | 2501.9(17) | 9180.8(17) | 5062.8(13) |
| C8 | 845.9(17) | 6216.7(17) | 7955.5(12) |
| C5 | 1781.3(16) | 5839.0(16) | 9808.8(12) |
| C10 | 826.8(17) | 6866.0(16) | 9543.4(13) |
| C6 | 2205.0(17) | 4998.2(16) | 9122.2(13) |
| C12 | 2080.2(17) | 8173.2(17) | 6012.1(13) |

TABLE 4-continued

Fractional Atomic Coordinates (×10⁴)

| Atom | x | y | z |
|---|---|---|---|
| C7 | 1754.4(17) | 5173.4(17) | 8190.5(13) |
| C14 | 589.4(16) | 8595.3(16) | 4410.3(13) |
| C9 | 357.9(17) | 7052.0(16) | 8617.5(13) |
| O3 | −2038.4(14) | 8080.4(13) | 2963.5(10) |
| C16 | −1279.0(17) | 7993.4(17) | 3694.5(13) |
| C19 | 94.2(16) | 7557.9(16) | 5365.3(12) |
| C18 | −1150.6(17) | 6755.4(17) | 5482.0(13) |
| C17 | −1821.6(17) | 6963.7(17) | 4673.3(13) |
| C15 | −97.9(17) | 8818.7(16) | 3570.7(13) |
| O4 | −3020.7(13) | 5254.0(13) | 4285.4(10) |
| O1 | 1664.4(14) | 7549.1(12) | 11211.0(11) |
| N2 | 2311.9(15) | 5606.3(13) | 10720.0(11) |
| C4 | 2272.8(17) | 6474.1(16) | 11345.7(13) |
| N4 | −4371.3(16) | 6291.1(16) | 5518.1(12) |
| C21 | −3137.7(18) | 6086.2(17) | 4805.1(13) |
| C20 | −1555(2) | 9072(2) | 1943.4(14) |
| C22 | 5454.7(19) | 1567.1(19) | 1285.1(15) |
| N1 | 2972.0(16) | 6034.4(14) | 12126.0(11) |
| C3 | 3082.9(19) | 6858.8(17) | 12805.7(13) |
| C1 | 4068(2) | 8090.2(18) | 12317.7(15) |
| O8 | 2287(3) | 10343.1(19) | 10576.9(16) |
| C2 | 4504(2) | 6911.5(19) | 13081.2(15) |

TABLE 5

Bond Lengths

| Atom | Atom | Length/Å |
|---|---|---|
| S1 | O5 | 1.4478(13) |
| S1 | O6 | 1.4715(12) |
| S1 | O7 | 1.4584(12) |
| S1 | C22 | 1.7586(18) |
| C12 | C6 | 1.7345(16) |
| O2 | C11 | 1.3356(19) |
| O2 | C8 | 1.4104(18) |
| N3 | C13 | 1.332(2) |
| N3 | C14 | 1.374(2) |
| C11 | C12 | 1.392(2) |
| C11 | C19 | 1.418(2) |
| C13 | C12 | 1.382(2) |
| C8 | C7 | 1.378(2) |
| C8 | C9 | 1.378(2) |
| C5 | C10 | 1.403(2) |
| C5 | C6 | 1.400(2) |
| C5 | N2 | 1.400(2) |
| C10 | C9 | 1.389(2) |
| C6 | C7 | 1.388(2) |
| C14 | C19 | 1.409(2) |
| C14 | C15 | 1.407(2) |
| O3 | C16 | 1.3442(19) |
| O3 | C20 | 1.439(2) |
| C16 | C17 | 1.430(2) |
| C16 | C15 | 1.378(2) |
| C19 | C18 | 1.415(2) |
| C18 | C17 | 1.362(2) |
| C17 | C21 | 1.511(2) |
| O4 | C21 | 1.230(2) |
| O1 | C4 | 1.228(2) |
| N2 | C4 | 1.377(2) |
| C4 | N1 | 1.353(2) |
| N4 | C21 | 1.331(2) |
| N1 | C3 | 1.430(2) |
| C3 | C1 | 1.497(2) |
| C3 | C2 | 1.489(2) |
| C1 | C2 | 1.495(3) |

TABLE 6

Bond Angles

| Atom | Atom | Atom | Angle/° |
|---|---|---|---|
| O6 | S1 | O5 | 112.55(8) |
| O7 | S1 | O5 | 113.44(8) |
| O7 | S1 | O6 | 110.85(7) |
| C22 | S1 | O5 | 106.45(8) |
| C22 | S1 | O6 | 105.91(8) |
| C72 | S1 | O7 | 107.09(9) |
| C8 | O2 | C11 | 118.48(12) |
| C14 | N3 | C13 | 122.23(14) |
| C12 | C11 | O2 | 124.98(14) |
| C19 | C11 | O2 | 114.73(13) |
| C19 | C11 | C12 | 120.29(14) |
| C12 | C13 | N3 | 122.24(14) |
| C7 | C8 | O2 | 118.06(14) |
| C9 | C8 | O2 | 119.25(15) |
| C9 | C8 | C7 | 122.49(15) |
| C6 | C5 | C10 | 117.47(14) |
| N2 | C5 | C10 | 123.73(14) |
| N2 | C5 | C6 | 118.80(14) |
| C9 | C10 | C5 | 120.74(15) |
| C5 | C6 | C12 | 119.32(12) |
| C7 | C6 | C12 | 118.08(12) |
| C7 | C6 | C5 | 122.57(15) |
| C13 | C12 | C11 | 117.96(15) |
| C6 | C7 | C8 | 117.49(15) |
| C19 | C14 | N3 | 118.30(14) |
| C15 | C14 | N3 | 120.17(14) |
| C15 | C14 | C19 | 121.53(14) |
| C10 | C9 | C8 | 119.19(15) |
| C20 | O3 | C16 | 118.23(13) |
| C17 | C16 | O3 | 114.24(13) |
| C15 | C16 | O3 | 125.35(15) |
| C15 | C16 | C17 | 120.39(15) |
| C14 | C19 | C11 | 118.94(14) |
| C18 | C19 | C11 | 122.61(14) |
| C18 | C19 | C14 | 118.45(14) |
| C17 | C18 | C19 | 120.39(15) |
| C18 | C17 | C16 | 120.56(14) |
| C21 | C17 | C16 | 119.72(14) |
| C21 | C17 | C18 | 119.71(14) |
| C16 | C15 | C14 | 118.62(15) |
| C4 | N2 | C5 | 126.30(14) |
| N2 | C4 | O1 | 123.45(15) |
| N1 | C4 | O1 | 122.82(15) |
| N1 | C4 | N2 | 113.73(14) |
| O4 | C21 | C17 | 120.54(14) |
| N4 | C21 | C17 | 114.58(14) |
| N4 | C21 | O4 | 124.88(15) |
| C3 | N1 | C4 | 119.98(14) |
| C1 | C3 | N1 | 118.38(14) |
| C2 | C3 | N1 | 118.40(15) |
| C2 | C3 | C1 | 60.08(12) |
| C2 | C1 | C3 | 59.68(12) |
| C1 | C2 | C3 | 60.24(12) |

TABLE 7

Hydrogen Atom Coordinates (A × 10⁴)

| Atom | x | y | z |
|---|---|---|---|
| H3 | 2070.5(15) | 10041.3(14) | 3738.1(11) |
| H13 | 3317.1(17) | 9732.7(17) | 4946.8(13) |
| H10 | 504.5(17) | 7428.3(16) | 9992.5(13) |
| H12 | 2599.8(17) | 8041.4(17) | 6528.7(13) |
| H7 | 2054.6(17) | 4607.7(17) | 7741.9(13) |
| H9 | −277.8(17) | 7732.1(16) | 8446.6(13) |
| H18 | −1512.4(17) | 6081.8(17) | 6114.7(13) |
| H15 | 237.7(17) | 9508.7(16) | 2945.3(13) |
| H2 | 2699.9(15) | 4848.0(13) | 10907.3(11) |
| H20a | −2141(11) | 8977(10) | 1481(5) |
| H20b | −1668(16) | 9946(2) | 2061.2(19) |
| H20c | −532(5) | 8953(10) | 1608(6) |
| H22a | 5185(8) | 1831(13) | 619(3) |

TABLE 7-continued

Hydrogen Atom Coordinates (A × 10⁴)

| Atom | x | y | z |
|---|---|---|---|
| H22b | 6386(4) | 1993(12) | 1192(8) |
| H22c | 5541(11) | 616(2) | 1488(6) |
| H1 | 3350.1(16) | 5259.2(14) | 12213.3(11) |
| H3a | 2179.1(19) | 6919.7(17) | 13371.2(13) |
| H1a | 4603(2) | 8276.2(18) | 11557.4(15) |
| H1b | 3752(2) | 8872.7(18) | 12575.0(15) |
| H2a | 4455(2) | 6982.4(19) | 13799.8(15) |
| H2b | 5305(2) | 6386.2(19) | 12782.6(15) |
| H4a | −4400(20) | 6850(20) | 5868(17) |
| H4b | −5170(30) | 5820(20) | 5635(17) |
| H8a | 2430(40) | 10660(40) | 11130(30) |
| H8b | 2160(40) | 9420(40) | 10830(30) |

Pharmacokinetics Studies

Example 9

After a single PO administration of Lenvantib Form XI, the plasma concentrations of Lenvantib reached the maximum concentration (mean (±SD) Cmax: 11543±2915 ng/mL) at a short Tmax of 0.833 h. and the observed extravascular mean (±SD) t½ was 1.95±0.04 h and was comparable to that after IV administration. Mean (±SD) AUCinf were 38914±11073 ng*h/mL, resulting in high absolute bioavailability (Fa) at 109%. The results showed that Lenvantib Form XI has higher systemic exposure and good absolute bioavailability after a signal oral administration, indicating Lenvantib is hardly affected by the first pass effect and is well absorbed in BALB/c mice.

All documents, including patents, patent application and publications cited herein, including all documents cited therein, tables, and drawings, are hereby expressly incorporated by reference in their entirety for all purposes.

While the foregoing written description of the compounds, uses, and methods described herein enables one of ordinary skill in the art to make and use the compounds, uses, and methods described herein, those of ordinary skill in the art will understand and appreciate the existence of variations, combinations, and equivalents of the specific embodiment, method, and examples herein. The compounds, uses, and methods provided herein should therefore not be limited by the above-described embodiments, methods, or examples, but rather encompasses all embodiments and methods within the scope and spirit of the compounds, uses, and methods provided herein.

The invention claimed is:

1. A crystalline form (Form XI) of 4-(3-chloro-4-(cyclopropylaminocarbonyl)aminophenoxy)-7-methoxy-6-quinolinecarboxamide methanesulfonate, characterized by an X-ray powder diffraction pattern comprising a peak at diffraction angle (2θ±0.2°) of 8.713°, wherein the X-ray powder diffraction pattern further comprises one or more peaks at diffraction angles (2θ±0.2°) selected from the group consisting of 10.366°, 12.819°, and 14.615°.

2. The crystalline form of claim 1, wherein the X-ray power diffraction pattern further comprising one or more peaks at diffraction angles (2θ±0.2°) selected from the group consisting of 9.520°, 19.400°, 20.218°, 22.895° and 26.876°.

3. The crystalline form of claim 1, wherein the crystalline form exhibits an X-ray powder diffraction pattern substantially as shown in FIG. 1.

4. The crystalline form of claim 1, wherein the crystalline form has an improved solubility as compared to Form A and Form C of 4-(3-chloro-4-(cyclopropylaminocarbonyl)aminophenoxy)-7-methoxy-6-quinolinecarboxamide methanesulfonate.

5. The crystalline form of claim 4, wherein the improved solubility is about 26.65 mg/mL.

6. The crystalline form of claim 1, which is a hydrate.

7. The crystalline form of claim 6, wherein the molar ratio of water to 4-(3-chloro-4-(cyclopropylaminocarbonyl)aminophenoxy)-7-methoxy-6-quinolinecarboxamide methanesulfonate is about 1:1.

8. A pharmaceutical composition comprising a crystalline form of claim 1, and an additive.

9. A process for preparing a crystalline form of claim 1, comprising the following steps:
   (i) dissolving 4-(3-chloro-4-(cyclopropylaminocarbonyl)aminophenoxy)-7-methoxy-6-quinolinecarboxamide methanesulfonate in a mixture of solvents to obtain a solution;
   (ii) adding an additional solvent into the solution obtained from step (i);
   (iii) stirring the resulting solution of step (ii) at room temperature for a period of time; and
   (iv) collecting the crystalline form.

10. The process of claim 9, wherein the mixture of solvents comprises water and acetonitrile.

11. The process of claim 9, wherein the additional solvent is ethyl acetate.

12. A method for treating cancer, wherein 4-(3-chloro-4-(cyclopropylaminocarbonyl)aminophenoxy)-7-methoxy-6-quinolinecarboxamide methanesulfonate is useful as a multiple-receptor tyrosine kinase (RTK) inhibitor in a subject in need thereof, comprising administering to the subject a therapeutically effective amount of a crystalline form of claim 1.

13. The method of claim 12, wherein the cancer is a thyroid cancer.

14. The method of claim 12, wherein the cancer is liver cancer.

15. The method of claim 12, wherein the cancer is renal cancer.

16. The pharmaceutical composition of claim 8, wherein the additive is a pharmaceutically acceptable excipient.

* * * * *